United States Patent [19]

Sheen et al.

[11] Patent Number: 5,676,015
[45] Date of Patent: Oct. 14, 1997

[54] CAVITATION CONTROLLED ACOUSTIC PROBE FOR FABRIC SPOT CLEANING AND MOISTURE MONITORING

[75] Inventors: Shuh-Haw Sheen; Hual-Te Chien, both of Naperville; Apostolos C. Raptis, Downers Grove, all of Ill.

[73] Assignee: The University of Chicago, Chicago, Ill.

[21] Appl. No.: 301,194

[22] Filed: Sep. 6, 1994

[51] Int. Cl.⁶ .................................................. G01N 5/02
[52] U.S. Cl. ............................................. 73/73; 73/159
[58] Field of Search .......................... 73/73, 866.5, 159, 73/592, 587, 596–598

[56] References Cited

U.S. PATENT DOCUMENTS

| | | | |
|---|---|---|---|
| 3,019,650 | 2/1962 | Worswick | 73/592 X |
| 3,595,070 | 7/1971 | Smith | 73/159 X |
| 3,664,191 | 5/1972 | Hermanns | 73/861.12 |
| 4,297,874 | 11/1981 | Sasaki | 73/73 |
| 4,674,325 | 6/1987 | Kiyobe et al. | 73/159 X |
| 5,092,168 | 3/1992 | Baker | 73/159 |
| 5,479,825 | 1/1996 | Williams et al. | 73/159 X |
| 5,576,480 | 11/1996 | Hoplins et al. | 73/587 X |

FOREIGN PATENT DOCUMENTS 5264442  10/1993  Japan ...................................... 73/73

OTHER PUBLICATIONS

1989 Ultrasonics Symposium, "Cavitation–Controlled Ultrasonic Agitator", Sheen, Lawrence and Raptis.

*Primary Examiner*—Elizabeth L. Dougherty
*Attorney, Agent, or Firm*—Joan Pennington

[57] ABSTRACT

A method and apparatus are provided for monitoring a fabric. An acoustic probe generates acoustic waves relative to the fabric. An acoustic sensor, such as an accelerometer is coupled to the acoustic probe for generating a signal representative of cavitation activity in the fabric. The generated cavitation activity representative signal is processed to indicate moisture content of the fabric. A feature of the invention is a feedback control signal is generated responsive to the generated cavitation activity representative signal. The feedback control signal can be used to control the energy level of the generated acoustic waves and to control the application of a cleaning solution to the fabric.

7 Claims, 2 Drawing Sheets

CAVITATION CONTROLLED ACOUSTIC PROBE FOR FABRIC SPOT CLEANING AND MOISTURE MONITORING

CONTRACTUAL ORIGIN OF THE INVENTION

The United States Government has rights in this invention pursuant to Contract No. W-31-109-ENG-38 between the United States Government and Argonne National Laboratory.

BACKGROUND OF THE INVENTION

1. Field of the Invention

The present invention relates to a method and apparatus for monitoring fabrics for moisture, and more particularly to an acoustic probe and process using the acoustic probe for monitoring fabrics for moisture and in dry cleaning the fabrics.

2. Description of the Prior Art

A need exists for an automated system for detecting moisture, oily spots or the like in the fabrics that is reliable and efficient. It is desirable to use such an automated system during the manufacture and processing of the fabrics to facilitate removal of the moisture and/or dry cleaning or fabric spot cleaning using little or no solvent. Development of cleaning systems using small amounts of cleaning solvents would aid the industry with respect to future EPA requirements. It is desirable to reduce the time required to process a fabric.

It is an object of the present invention to provide an improved method and apparatus for monitoring fabrics for moisture.

It is another object of the present invention to provide an improved method and apparatus for monitoring moisture in a fabric using an acoustic probe.

It is another object of the present invention to provide an improved method and apparatus for monitoring moisture in a fabric using an acoustic probe to provide dry cleaning or fabric spot cleaning using little or no solvent.

It is another object of the present invention to provide an improved method and apparatus for monitoring moisture in a fabric overcoming some of the disadvantages of known arrangements for fabric cleaning.

SUMMARY OF THE INVENTION

In brief, these and other objects and advantages of the invention are provided by a method and apparatus for monitoring a fabric. An acoustic probe generates acoustic waves relative to the fabric. An acoustic sensor, such as an accelerometer is coupled to the acoustic probe for generating a signal representative of cavitation activity in the fabric. The generated cavitation activity representative signal is processed to indicate moisture content of the fabric. A feature of the invention is that a feedback control signal is generated responsive to the generated cavitation activity representative signal. The feedback control signal can be used to control the energy level of the generated acoustic waves and to control the application of a cleaning solution to the fabric.

BRIEF DESCRIPTION OF THE DRAWING

These and other objects and advantages of the present invention will become readily apparent upon consideration of the following detailed description and attached drawing, wherein.

DETAILED DESCRIPTION OF THE PREFERRED EMBODIMENT

Figure 1:
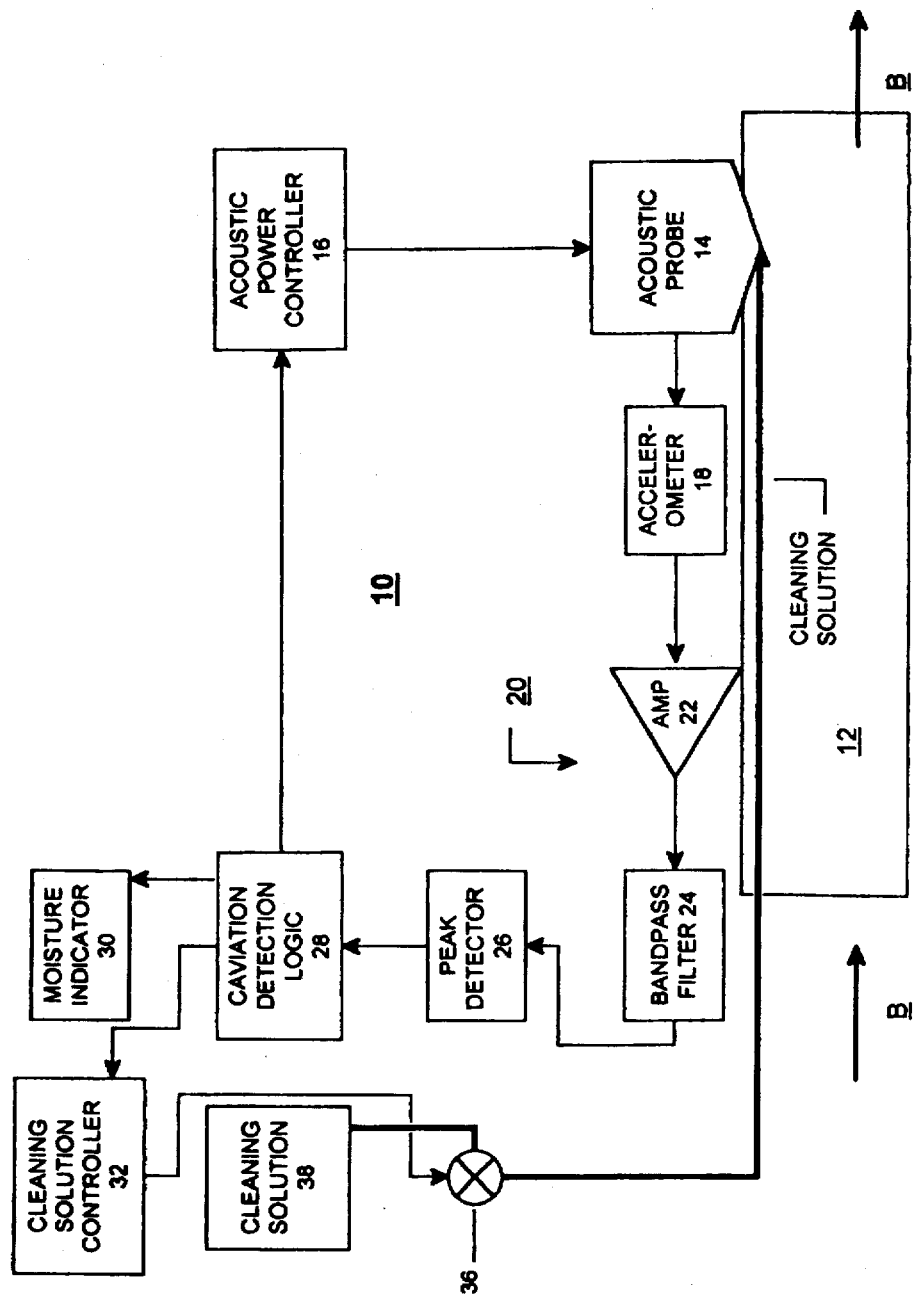
FIG. 1 is a schematic and block diagram representation of a fabric monitoring system of the invention.

Referring to FIG. 1 of the drawing, there is shown a schematic and block diagram representation of a fabric monitoring system according to the invention generally designated by the reference numeral 10. Fabric monitoring system 10 is a simple, low cost arrangement. Fabric monitoring system 10 is used to detect moisture content of a fabric 12 to provide an indication of the moisture content of the fabric and also can be used to provide corrective spot cleaning of the fabric.

Fabric monitoring system 10 includes an acoustic probe 14 operatively controlled by an acoustic power controller 16, an accelerometer 18 attached to the acoustic probe 14 for detecting cavitation activity and feedback and control signal processing circuitry generally designated by the reference numeral 20. Acoustic probe 14 is a high-power acoustic probe advantageously used in textile processing. When large-amplitude acoustic waves propagate in a liquid, non-linear acoustic effects such as cavitation occur. Cavitation may cause liquid evaporation and induce chemical reactions. The cavitation effects resulting from use of the acoustic probe 14 on a fabric 12 include liquid evaporation, loosening of the foreign material representing a spot and/or some chemical reactions could occur. Close monitoring of cavitation activity provides control for an acoustic cleaning process and a detection of moisture content in a fabric material. A commercially available accelerometer or a piezoelectric ceramic sensor can be used for the accelerometer 18.

Feedback and control signal processing circuitry 20 includes the accelerometer 18 for detecting cavitation activity which is typically indicated by the presence of subharmonics. The accelerometer output signal is applied to a pre-amplifier 22 and amplified. The amplified signal is applied to a bandpass filter 24. Then peak amplitudes are measured from the filtered signal at a peak detector block 26. Peak amplitude values are applied to a caviation detection logic block 28. The caviation detection logic block 28 generates a feedback control signal that is applied to the acoustic power controller 16, for example to control the output power according to the amount of moisture remaining in fabric.

Caviation detection logic block 28 detects subharmonics and generates a signal representing the detected moisture content in a fabric 12 that is applied to a moisture indicator block 30. Caviation detection logic block 28 generates a control signal that is applied to a cleaning solution controller 32. A valve 36 controls flow from a cleaning solution supply 38 via a conduit indicated by a line labelled CLEANING SOLUTION and a nozzle indicated by an arrow labelled A to the fabric 12. Valve 36 is operatively controlled by the cleaning solution controller 32 responsive to the applied control signal from the caviation detection logic block 28. For spot cleaning, a small amount of cleaning solution is applied to the fabric 12 at a rate proportional to the cavitation signals identified by the caviation detection logic block 28. The fabric can be moving as indicated by an arrow B. The acoustic probe 14 with the attached cleaning solution nozzle A can be moved around to provide spot cleaning. The rate of injecting cleaning solution is controlled by the cavitation signals which generally appear as the subharmonics of the probe frequency. The selection of cleaning solution will be determined by the type of spots to be cleaned.

Figure 2:
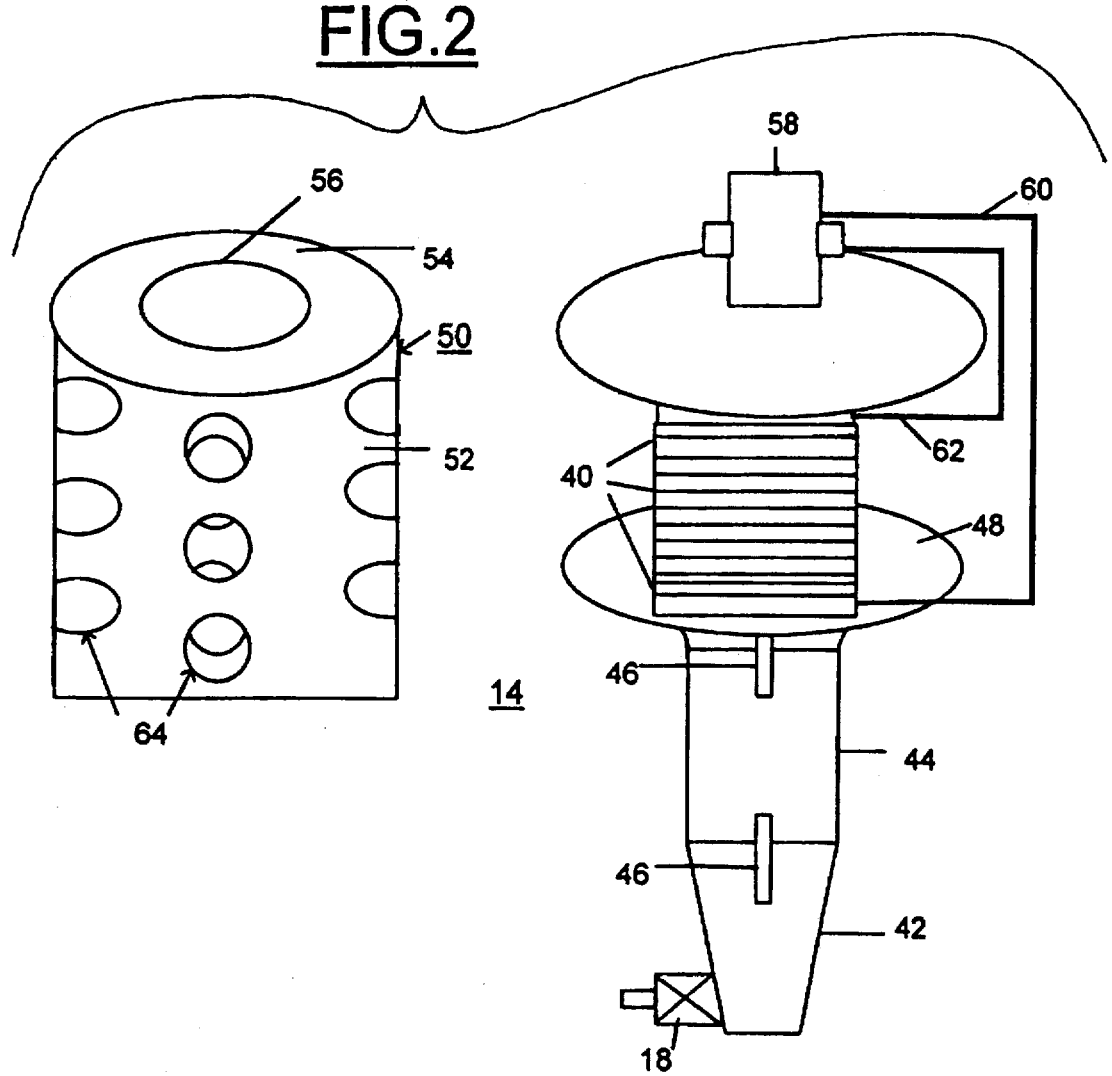
FIG. 2 is a perspective view of an acoustic probe and a probe housing removed from the acoustic probe of the fabric monitoring system of FIG. 1.

As shown in FIG. 2, the acoustic probe 14 includes a stack of hollow piezoelectric ceramics 40 that generate high-power longitudinal waves of frequency below 40 KHz and a horn-shaped waveguide 42 coupled to the piezoelectric ceramic by a booster 44. Waveguide 42 focuses acoustic energy generated by the piezoelectric ceramics 40 to a small area. The accelerometer 18 is attached near a tip 46 of the waveguide 42 for detecting the cavitation signals. A pair of mounting studs 46 mount waveguide 42 to the booster 44 and the booster to a support 48 that supports the stack of piezoelectric ceramics 40. A housing generally designated by the reference character 50 includes a cylindrical body 52 defining a cavity for receiving the stack of piezoelectric ceramics 40. An upper surface 54 of the housing 50 includes an aperture 56 for receiving a connector 58. Connector 58 is mounted on the support 48. Connector 58 is connected to a negative lead 60 and a positive lead 62 connected to opposed ends of the stack of piezoelectric ceramics 40 for coupling an electrical signal to or from the stack of piezoelectric ceramics. A plurality of apertures 64 are provided in the housing body 52 to facilitate air flow and cooling of the stack of piezoelectric ceramics 40.

The stack of piezoelectric ceramics 40 may be formed by piezoelectric lead zirconate titanate (PZT-4) rings mounted by the support 48. Waveguide 42 and booster 44 can be formed of mild steel having appropriate dimensions for resonant frequency as determined by the operating frequency of the stack of piezoelectric ceramics 40.

In brief summary, the fabric monitoring system 10 with the acoustic probe 14 can effectively remove oil, paint and other spots from fabric 12. The acoustic spot cleaning is fast and saves energy as compared to conventional cleaning arrangements. Fabric monitoring system 10 can be used for spot cleaning of cloth and fabrics during processing and potentially reduce use of conventional cleaning solutions which are environmentally hazardous.

Obviously, many modifications and variations of the present invention are possible in light of the above teachings. Thus, it is to be understood that, within the scope of the appended claims, the invention may be practiced otherwise than as specifically described above.

What is claimed and desired to be secured by Letters Patent of the United States is:

1. Apparatus for monitoring a fabric comprising:
   acoustic probe means for generating acoustic waves relative to the fabric; wherein said acoustic probe means includes a stack of piezoelectric ceramics for generating acoustic longitudinal waves having a predetermined frequency and wherein said predetermined frequency is less than 40 Khz; wherein said acoustic probe means includes a horn-shaped waveguide and; wherein said horn-shaped waveguide is coupled to said stack of piezoelectric ceramics by a booster member;
   acoustic sensor means coupled to said acoustic probe means for generating a signal representative of cavitation activity in the fabric; and
   signal processing means responsive to said acoustic sensor means for processing said generated signal to indicate moisture content of the fabric.

2. Apparatus for monitoring a fabric as recited in claim 1 wherein said stack of piezoelectric ceramics is mounted within a housing.

3. Apparatus for monitoring a fabric as recited in claim 1 wherein said acoustic probe means includes a positive lead and a negative lead connected to opposed ends of said stack of piezoelectric ceramics.

4. Apparatus for monitoring a fabric comprising:
   acoustic probe means for generating acoustic waves relative to the fabric;
   acoustic sensor means coupled to said acoustic probe means for generating a signal representative of cavitation activity in the fabric;
   signal processing means responsive to said acoustic sensor means for processing said generated signal to indicate moisture content of the fabric; wherein said signal processing means further includes feedback control means coupled to said acoustic sensor means for generating a control signal related to said moisture content of the fabric; and
   cleaning solution controller means for controlling cleaning solution applied to the fabric responsive to said generated control signal.

5. Apparatus for monitoring a fabric as recited in claim 4 wherein said signal processing means include a peak detector coupled to said accelerometer and cavitation detection logic coupled to said peak detector for generating said control signal.

6. Apparatus for monitoring a fabric comprising:
   acoustic probe means for generating acoustic waves relative to the fabric;
   acoustic sensor means coupled to said acoustic probe means for generating a signal representative of cavitation activity in the fabric; and
   signal processing means responsive to said acoustic sensor means for processing said generated signal to indicate moisture content of the fabric; wherein said signal processing means further includes feedback control means coupled to said acoustic sensor means for generating a control signal related to said moisture content of the fabric; wherein said feedback control means includes means for generating a control signal for controlling an energy level of said generated acoustic waves proportional to a detected moisture content of the fabric.

7. A method for monitoring a fabric with a fabric monitoring system including a high power acoustic probe comprising the steps of:
   generating acoustic waves relative to the fabric;
   detecting cavitation activity and generating a signal;
   processing said generated signal to indicate moisture content of the fabric; wherein said step of processing said generated signal includes the step of identifying amplitude peaks of said generated signal and converting said identified amplitude peaks to a control signal applied to the high power acoustic probe; and
   controlling a cleaning solution being applied to the fabric responsive to said generated control signal.

* * * * *